US008425918B2

(12) United States Patent
Hutás

(10) Patent No.: US 8,425,918 B2
(45) Date of Patent: Apr. 23, 2013

(54) USE OF EDTA AND ITS DERIVATIVES FOR PREVENTION AND TREATMENT OF BACTERIAL INTESTINAL DISEASES OF PIGS AND FOR INCREASING THE EFFECTS OF ANTIBIOTICS EXERTED IN SUCH DISEASES

(75) Inventor: István Hutás, Budapest (HU)

(73) Assignee: Pharmatéka Gyártó és Kereskedelmi BT, Budapest (HU)

( * ) Notice: Subject to any disclaimer, the term of this patent is extended or adjusted under 35 U.S.C. 154(b) by 274 days.

(21) Appl. No.: 12/743,791

(22) PCT Filed: Sep. 25, 2008

(86) PCT No.: PCT/HU2008/000105
§ 371 (c)(1),
(2), (4) Date: May 19, 2010

(87) PCT Pub. No.: WO2009/066117
PCT Pub. Date: May 28, 2009

(65) Prior Publication Data
US 2010/0284994 A1   Nov. 11, 2010

(30) Foreign Application Priority Data
Nov. 22, 2007  (HU) .................................... 0700745

(51) Int. Cl.
*A61K 39/02*      (2006.01)
*C07C 229/00*   (2006.01)

(52) U.S. Cl.
USPC ........ 424/262.1; 562/566; 536/16.8; 424/825

(58) Field of Classification Search ............... 424/262.1, 424/825; 562/566; 536/16.8
See application file for complete search history.

(56) References Cited

U.S. PATENT DOCUMENTS

| 4,716,173 A | 12/1987 | Salatinjants |
| 2003/0194451 A1 | 10/2003 | Cho et al. |

FOREIGN PATENT DOCUMENTS

| CN | 1434007 A | 8/2003 |
| EP | 0005346 A1 | 11/1979 |
| EP | 0597167 A1 | 5/1994 |
| GB | 2027590 A | 2/1980 |
| WO | 2004/080210 A1 | 9/2004 |

OTHER PUBLICATIONS

Duhamel et al. (G85-748 Prevention and control of Swine dysentery, Nebguide, Apr. 1991, pp. 1-6.*
Novotna et al. Vet-Med.-Czech 47, 2002 (4): 104-109.*
Obiso, Richard J. Jr. et al., "Proteolytic Activity of the Bacteroides fragilis Enterotoxin Causes Fluid Secretion and Intestinal Damage In Vivo," Infection and Immunity, vol. 63, No. 10, pp. 3820-3826 (Oct. 1995).

* cited by examiner

*Primary Examiner* — Savitha Rao
(74) *Attorney, Agent, or Firm* — Speckman Law Group PLLC; Janet Sleath

(57) ABSTRACT

The invention relates to the use of ethylenediamine tetraacetic acid (EDTA) and its derivatives, i.e. its salts and complexes for prevention and treatment of bacterial intestinal diseases of pigs and for increasing the effects of antibiotics exerted in such diseases. The invention also relates to compositions for animal husbandry, i.e. to veterinary compositions and to feeds and drinks which can be consumed by pigs, comprising EDTA or its derivatives.

8 Claims, No Drawings

USE OF EDTA AND ITS DERIVATIVES FOR PREVENTION AND TREATMENT OF BACTERIAL INTESTINAL DISEASES OF PIGS AND FOR INCREASING THE EFFECTS OF ANTIBIOTICS EXERTED IN SUCH DISEASES

REFERENCE TO RELATED APPLICATIONS

This application is the US national phase entry of International Patent Application No. PCT/HU2008/000105, filed Sep. 25, 2008, which claims priority to Hungarian Application No. P 0700745, filed Nov. 22, 2007.

BACKGROUND

The invention relates to the use of ethylenediamine tetraacetic acid (further on: EDTA) and its derivatives, i.e. its salts and complexes for prevention and treatment of bacterial intestinal diseases of pigs and for increasing the effects of antibiotics exerted in such diseases. The invention also relates to compositions for animal husbandry comprising EDTA or its derivatives. The term "composition for animal husbandry" encompasses both veterinary compositions and feeds and drinks which can be consumed by pigs, such as fodders, feeds, nutriments, pre-mixes and drinking water additives.

Of the bacterial diseases of pigs pig dysentery is the one which causes the most serious problems. Pig dysentery is an epizootic disease of piglets and grown-up pigs involving mucous-bloody diarrhoea and furfuraceous necrosis of colonic mucous membrane.

Pig dysentery belongs to diseases which frequently occur all over the world. Due to the direct losses and to the high costs of therapy this disease causes considerable economic damages. The causative pathogen of the disease is Brachyspira hyodysenteriae, previously also termed as Treponema hyodysenterae or Serpulina hyodysenteriae. The resistance of the pathogen is low; it dies within some minutes at temperatures exceeding 60° C. and upon the effect of conventional disinfecting agents and it dies within some days upon drying. However, the bacteria remain viable in the mucous-bloody faeces in summer for at least one week and in winter even for about two months. In thin manure which forms in large amounts at pig farms, the pathogen may be viable even for some months. Pigs are susceptible to the pathogen, moreover the pathogen may also accumulate in the intestines of rats, mice and dogs living at the infected farm. The pathogen is excreted by rats for some days, by dogs for some weeks, and mice may excrete the pathogen even for some months.

The disease is observed generally on pigs older than 6-8 weeks, because suckling pigs have usually maternal immunity. Immunity developed in older pigs is poor and partial. Upon a massive re-infection or as a result of farming anomalies the disease may re-develop on one and the same livestock. Despite the acquired relative immunity, most of the once-recovered pigs remain carriers and excreters of the pathogen even during their entire lifespan.

The pathogen binds to the surface of intestinal endothelial cells but does not enter them. The toxins which liberate from the bacteria damage the endothelial cells of the mucous membrane, as a result of which the endothelial cells die and inflammation sets in. This inflammation induces excessive mucus production, bleeding occurs, liquid is excreted into the intestinal cavities, a severe diarrhoea sets in, the absorption potential of the intestines is severely impaired, followed by the necrosis of the surface layer of the intestinal mucous membrane. The lesions are throughout restricted to the colon.

The latency period is 10-14 days. The first symptom is a water-like diarrhoea coupled with subfebrility and lack of appetite. After some days blood and fibrin shreds also appear in the faeces. At this time faeces is already chocolate brown. The animals get weakened, they do not eat only drink, and their body weight rapidly decreases. Many of the animals die; the perishment ratio may be as high as 30%. Although the majority of the sick animals recovers, their development gets retarded and they continue to excrete the pathogen.

Beside the characteristic symptoms, necropsy usually shows a repleted stomach and a swollen hyperaemic mucous membrane covered with phlegm. The mucous membrane of the colon is swollen, bright red, particularly at the edges of the folds, and has a velvet-like surface. At a later stage a furfuraceous deposit appears due to the necrosis of the surface of the mucous membrane.

Numerous veterinary substances and compositions have already been used for the treatment of bacterial intestinal disesases of pigs, particularly of pig dysentery. Examples of them are various sulfonamides, benzene-acetonitrile, benzoic acid, pyridine, quinoline, pyrimidine and guanidine derivatives, as well as ionophoric antibiotics which have become increasingly frequent in the last decades. The use of some of the known active agents which proved to be effective, thus e.g. carbadox and dimetridazole, is nowadays not allowed due to the long stay periods prescribed by food hygienics and/or due to the disadvantages to human health detected in the meanwhile. The pathogen develops resistance relatively quickly against some active agents, particularly against guanidine derivatives and antibiotics. As a particular problem, the known active agents can frequently be used only for the treatment of an already established disease but not for prevention, or if yes, their prolonged use lays an undue burden on the animal organism and sometimes runs with undesired side effects. Vaccination did not prove to be successful against the disease.

SUMMARY

Therefore, there exists a need for a composition which fulfils simultaneously the following requirements:
- beside a quick and effective therapy of the disease it can also be used for prevention;
- when administered to slaughter animals no or only a short food hygienic stay period is required;
- the pathogens do not develop resistance against the composition;
- no human health consideration appears in connection with its use;
- it is fully harmless to the animal organism even upon a prolonged administration and does not cause undesired side effects or tolerance problems.

Now we have found, unexpectedly, that EDTA and EDTA salts and complexes acceptable for animal health care purposes (further on: EDTA derivatives) fully meet the above criteria.

We have also found as a new recognition that EDTA and the above EDTA derivatives significantly increase the activity of antibiotics (e.g. of lincomycin, tiamulin) used before in the treatment of bacterial intestinal diseases of pigs, and upon a combined treatment no resistance develops in the pathogen or development of any resistance is delayed.

EDTA and its salts are commonly known analytical chemicals, and some human medical effects of them have also been reported. EDTA and its alkali metal salts, when added parenterally, are applicable against acute and chronic metal poisonings [Issekutz: Gyógyszerrendelés p. 480 (Medicina Könyvkiadó, Budapest, Hungary, 1978); Am. J. Ind. Med. 33

(1985)], and, due to their C-protein kinase inhibiting effect, they can also be used in the treatment of cardiac and circulation diseases, diseases of the central nervous system, inflammation processes, cancer and viral infections (Hungarian Patent No. 204 195). Alkali metal salts of EDTA, when combined with menthol and camphor, can be used in the topical treatment of rheumatic pains (Hungarian Patent No. 207 446). In veterinary alkali metal salts of EDTA are used in topical compositions for wound treatment to solubilize zinc oxide, a well known would healing agent. EDTA also appears in low concentrations in some pharmaceutical products as a stabilizing additive, primary to protect metal sensitive components. We have not found, however, any reference to that EDTA would exert any effect on the pathogens of intestinal diseases of pigs and would have any influence on the activities of antibiotics applicable in the treatment of such diseases.

Based on the above, the invention relates to the use of EDTA and to salts and complexes of EDTA acceptable for animal health care purposes for prevention and/or treatment of bacterial intestinal diseases of pigs and/or for increasing the activities of antibiotics applicable in the treatment of such diseases.

For these purposes EDTA and the above EDTA derivatives are administered to the animals internally, particularly preferably by oral route.

Furthermore, the invention relates to a composition for animal husbandry, also encompassing veterinary compositions, for administering to pigs, which comprises as active agent EDTA or a salt or complex of EDTA acceptable for animal health care purposes, together with the conventional componens (e.g. carriers, other auxiliary agents and/or activity-complementing agents) of the composition concerned and optionally together with an antibiotic applicable in the treatment of bacterial intestinal diseases of pigs.

The term "composition for animal husbandry" as used in the present description and claims encompasses the full choice of veterinary compositions for internal administration and feeds and drinks which can be consumed by pigs. Thus, beside the classical veterinary dosage forms for internal administration (particularly preferred representatives of which are orally administerable dosage forms, such as pastes, solutions, tablets, etc.) the compositions for animal husbandry may also be medicated fodders, feeds, nutriments, premixes, drinking waters and drinking water additives. As EDTA and its derivatives are used generally in mass animal husbandry to prevent bacterial intestinal diseases of pigs, particularly pig dysentery, or for the therapy of an already established disease, particularly preferred forms of the compositions for animal husbandry are fodders, feeds, nutriments and premixes complemented with EDTA or with an EDTA derivative, and drinking water comprising a water-soluble EDTA derivative.

The concentration of EDTA or of an EDTA derivative in a composition for animal husbandry depends on numerous factors, among others on the purpose to be attained (prevention or therapy), on the severity of the already established disease and on the type of the composition for animal husbandry concerned.

Foods and fodders for direct consumption may comprise usually 30-720 g, preferably 100-500 g, more preferably 250-350 g of EDTA or an equivalent amount of an EDTA derivative for 1 ton of food or fodder. The active agent content of a food or fodder to be used for prevention is usually lower than those to be used for the treatment of an already established disease.

The active agent content of a nourishment, which is usually fed to the animals as a complement of the fodder, may be the 2-20 fold of the values indicated above. The active agent of a premix should be increased according to its mixing ratio with the fodder or nourishment; the active agent content of a premix may be e.g. 10-100 fold of the values indicated above.

In veterinary compositions for direct oral administration and in fodders, feeds, nourishments and premixes it is particularly preferred to use an EDTA derivative with restricted water solubility or a water soluble EDTA derivative together with a solubility-lowering additive. Examples of the latter compositions are those which comprise sodium salts of EDTA together with an acid, primarily together with an organic acid. The advantage of these compositions over those comprising water soluble active agents alone is that the organic acid component strengthens the surface of the mucous membrane, making it unsuitable for settling of the pathogenic bacteria. Fodders or suspensions (drench compositions) which comprise either poorly water soluble EDTA derivatives or a solubility-lowering additive are excreted at a lower rate from the intestinal tract of the animals, thus they exert their antibacterial effects for a prolonged period of time. In other words, upon admixing an EDTA salt with good water solubility together with an agent acceptable for animal health purposes which forms a precipitate with EDTA in water the activity of the composition can be increased and prolonged. Gallic acid and tannic acid are particularly suitable representatives of these additives. For this purpose e.g. plant extracts comprising tannic acid (such as a chestnut extract marketed under the name Farmatán$^{(R)}$) and synthetic preparations can be admixed.

The orally administerable compositions for animal husbandry may also be drinking water additives, which may also comprise, beside the active agent, optionally one or more diluent, auxiliary agent and/or activity-complementing agent acceptable for animal health purposes. Obviously, these compositions may comprise only an active agent which can be dissolved in the drinking water in the final concentration to be attained (for the prevention or treatment of pig dysentery this may be e.g. 10-350 g of EDTA or an equivalent amount of an EDTA derivative calculated for 1000 liters of water). In order to increase the accuracy of active agent administration it is preferred to use the active agent in a drinking water additive as a mixture with a diluent acceptable for animal health care purposes.

The term "activity-complementing agent(s)" which can be used together with EDTA or with an EDTA derivative refers to substances which have already been used in animal husbandry to attain various beneficial results but which proved to be ineffective or of low effectivity in the treatment of bacterial intestinal diseases of pigs, with the exception of the antibiotics mentioned above. Of these activity-complementing agents those utilized before as appetizers, as agents for increasing fodder utilization, as immunostimulants and/or as agents for the protection of the intestinal tract are particularly preferred. These agents additionally might have some antibacterial effect. Particularly preferred representatives of activity-complementing agents are the following substances:

Essential (etheral) oils: Due to their appetizing effects they increase both fodder consumption and digesting liquor secretion. They also exert a positive bacteriostatic (i.e. propagation-inhibiting) effect against anaerobic bacteria, but show hardly any effect against the bacterial causatives of intestinal diseases of pigs. They can be used without any restriction for foddering purposes and can be admixed with oral veterinary compositions, fodders for direct consumption and, depending on their water solubility, with drinking water.

Tannic acid: It strengthens the intestinal mucous membrane, produces a protective deposit on it, restricting thereby the absorption of harmful.sbstances. When diarrhoea has already been established, its effects exerted on the mucous membrane result in a decrease of phlegm excreted into the intestinal cavities. Due to its slight bactericidal effects it has a favourable influence on the composition of intestinal flora. It can be used without any restriction for foddering purposes. As tannic acid forms a precipitate with EDTA and with its water soluble salts, it can be added only to solid compositions or to suspensions but not to drinking water.

Lysosime (muramidase) enzyme: It is a bacteriolytic enzyme produced both in human and in animal organism which increases the resistance of living organism, stimulates the immune system and also exerts phlegm decomposing, tissue recovery increasing, haemostatic and virus and tumor growth inhibiting effects. It is a usual component of several veterinary compositions. It can be used for foddering purposes without any restriction and can also admixed with drinking water.

The active agents can be introduced into compositions for animal husbandry by any of the conventional techniques. As the required active agent content of fodders and nutriments for direct consumption is of the ppm order (mg/kg), it is preferred to prepare first a premix of high active agent content, which is diluted then to obtain the final fodder or nutriment. According to an alternative method an aqueous solution comprising the active agent in an appropriate concentration is sprayed onto the grainy or fibrous fodder.

As it has already been mentioned, EDTA and its derivatives as defined above also increase the activity of antibiotics applicable for the treatment of bacterial intestinal diseases of pigs. Therefore, beside the prevention or treatment of bacterial intestinal diseases of pigs, administration of a composition for animal husbandry which contains EDTA or an EDTA derivative is also very useful when in parallel the pigs also receive a targeted antibiotic treatment.

Upon the parallel administration of EDTA or of an EDTA derivative as defined above the dose of antibiotic required in the treatment of the disease can be lowered and/or the period of antibiotic treatment can be shortened.

The required amount of antibiotic can also be introduced into the composition for animal husbandry comprising EDTA or an EDTA derivative, but the antibiotic can also be administered to the animal as a separate composition. In this latter event EDTA and the antibiotic may also be administered in different ways; e.g. EDTA may be administered orally and the antibiotic may be administered parenterally.

When antibiotic treatment of pigs is combined with the administration of EDTA or an EDTA derivative, the required dose of the antibiotic may be 25-100% of the otherwise required one (when the total amount of the otherwise required dose of antibiotic is administered, the duration of treatment can be shortened). The required concentration of an antibiotic in a composition comprising both antibiotic and EDTA or an EDTA derivative can be calculated on this basis.

DETAILED DESCRIPTION

Further details of the invention are illustrated in the following Examples.

EXAMPLE 1

Premix for Mixing with a Pig Fodder

Composition of the premix:

| | |
|---|---|
| BFF 55 wheat flour ("strudel" grade) | 61.6 kg |
| Farmatán 70% (tannic acid-comprising composition sold by Dakovit Kft, Györ, Hungary) | 10 kg |
| Thyme oil | 1.4 kg |

-continued

| | |
|---|---|
| Emulson (emulsifying agent sold by WMD Kft, Budapest, Hungary) | 2.2 kg |
| Oregano oil | 0.8 kg |
| EDTA $Na_2$ salt | 24 kg |

The BFF 55 wheat flour, the Farmatán 70% and the EDTA $Na_2$ salt were weighed in the given order into a TUK 400 liter/200 kg mixer and the components were homogenized by stirring for 2 minutes. The essential oils were admixed separately with the Emulson, the liquid mixture was added through a funnel to the powder mixture obtained in the previous step, and the mass was homogenized by stirring for 2 minutes.

EXAMPLE 2

Pig Fodder for Direct Consumption 2 kg of a premix with the composition as given in Example 1 was homogenized with 18 kg of a fodder of similar grain size, and this 20 kg mixture was admixed with 1980 kg of a fodder. Fodders of the following compositions were prepared:

| | Amount, % | |
|---|---|---|
| Component | For piglets | For porkers |
| Maize | 43.61 | 47.73 |
| Rice protein | 2.10 | |
| Fat powder 40% | 2.60 | 2.60 |
| Bran | 5.00 | 4.30 |
| Barley | 15.00 | 15.00 |
| Wheat | 8.60 | 5.00 |
| Soybean | 16-60 | 17.10 |
| Ground sunflower | 3.00 | 5.00 |
| Fodder grade lime | 1.20 | 1.27 |
| Monocalcium phosphate | 0.82 | 0.80 |
| Fodder grade salt | 0.40 | 0.40 |
| Lysine | 0.27 | 0.27 |
| Piglet/porker premix* | 0.50 | 0.40 |
| Ultracid | 0.20 | 0.20 |
| Premix according to Example 1 | 0.10 | 0.10 |

*Product of Fiorács Kft (Ács, Hungary)
**A phosphoric acid-containing product of Syngenta Ltd.

EXAMPLE 3

Premix for Mixing to Drinking Water of Pigs

Composition of the premix:

| | |
|---|---|
| Dextrose | 75.0 kg |
| Lysosime HCl | 10.0 kg |
| Thyme oil | 0.7 kg |
| Emulson | 2.0 kg |
| Oregano oil | 0.3 kg |
| EDTA $Na_2$ salt | 12.0 kg |

The dextrose, the lysosime HCl and the EDTA $Na_2$ salt were weighed in the given order into a TUK 400 litre/200 kg mixer and the components were homogenized by stirring for 2 minutes. The essential oils were admixed separately with the Emulson, the liquid mixture was added through a funnel to the powder mixture obtained in the previous step, and the mass was homogenized by stirring for 2 minutes.

EXAMPLE 4

Suspension for Oral Administration (Drench)

A suspension of the following composition was prepared by mixing the individual components:

| | |
|---|---|
| EDTA Na$_2$ salt | 25.00 kg |
| Menthol | 0.01 kg |
| Mucilago hydroxyaethylcellulosum | 74.00 kg |
| Emulson | 1.00 kg |

EXAMPLE 5

Testing of Compositions Comprising EDTA on Pigs Suffering from Bloody Diarrhoea (Brachyspira Infection)

EXAMPLE 5.1

On a pig farm infected with the pathogen 3 test groups of 20 animals each and one control group of 20 animals were formed from 90 days old piglets. The fodder of the animals belonging to the test groups was complemented throughout the test period (which lasted to slaughtering) with 240 ppm of EDTA Na$_2$ salt utilizing the premix as described in Example 1. No bloody diarrhoea appeared on the animals belonging to the test groups. In contrast to the other animals of the farm, no antibiotic treatment of the the animals of the test groups was required.

EXAMPLE 5.2

Pigs suffering from bloody diarrhoea, husbanded on the farm according to Example 5.1, were treated with EDTA Na$_2$ in such a way that 200 ppm of EDTA Na$_2$ were dissolved in the drinking water of the animals. Bloody diarrhoea ceased on the third day and did not reoccur while the presence of 200 ppm of EDTA Na$_2$ was maintained in the drinking water. In the control group where on the day following the cease of diarrhoea the animals were returned to drinking of pure water bloody diarrhoea reappeared after 4 days.

EXAMPLE 5.3

At a pig farm infected with the pathogen a nourishment comprising 110 ppm of lincomycin was fed with the livestock suffering from bloody diarrhoea. A part of the livestock showed resistance against the antibiotic. The livestock was separated proportionally, and in the test group 240 ppm of EDTA Na$_2$ salt was admixed to the nourishment, utilizing the premix according to Example 1. In this group bloody diarrhoea completely ceased on the third day. When continuing feeding with a fodder comprising EDTA Na$_2$ salt no bloody diarrhoea occurred on these animals later on. In the control group bloody diarrhoea still persisted, and it ceased only when the lincomycin treatment had been completed with another effective antibiotic treatment.

EXAMPLE 5.4

In a part of the lincomycin-resistant animals belonging to the livestock according to Example 5.3, no treatment with another antibiotic was performed, but lincomycin therapy was maintained and simultaneously drinking water comprising 60 ppm of EDTA Na$_2$ was added to the animals. Diarrhoea ceased completely within some days and it did not reoccur after terminating the lincomycin treatment while the administration of EDTA Na$_2$ into the drinking water was continued. No pathogenic bacteria could be detected in the faeces, either.

EXAMPLE 5.5

At a pig farm with frequently occurring bloody diarrhoea three groups were formed randomly from weaned piglets at switching to solid nourishment. In the first group (test group) the animals were fed continuously with a nourishment comprising 240 ppm of EDTA Na$_2$, 22 ppm of essential oils (1:1 mixture of oregano oil and thyme oil) and 100 ppm of tannic acid. In the second group (control group 1) the animals were fed continuously with a nourishment comprising essential oils and tannic acid in the above amounts but free of EDTA Na$_2$. In the third group (control group 2) no EDTA Na$_2$, essential oils or tannic acid were added to the nourishment of the animals.

After a certain period of time soft faeces and then bloody diarrhoea appeared in the animals of control group 2 (fed with a nourishment without completion). Bacteria of Brachospira type were detected in the faeces. In the animals of control group 1 (fed with a nourishment complemented with essential oils and tannic acid) soft faeces and bloody diarrhoea appeared with a delay. In contrast thereto, in the animals belonging to the test group (fed with a nourishment also comprising EDTA Na$_2$) no abnormal biological symptom could be observed while they consumed the thus-complemented nourishment.

The invention claimed is:

1. A method for prevention and/or treatment of pig dysentery caused by Brachyspira hyodysenteriae, comprising administering to a pig ethylenediamine tetraacetic acid or a salt thereof acceptable for animal health care purposes.

2. A method for increasing activity of an antibiotic applicable in the treatment of pig dysentery caused by Brachyspira hyodysenteriae, comprising administering to a pig the antibiotic and ethylenediamine tetraacetic acid or a salt thereof acceptable for animal health care purposes.

3. A composition according to claim 1, further comprising administering to the pig an antibiotic selected from the group consisting of: lincomycin and tiamulin.

4. The method of claim 1, wherein the salt of ethylenediamine tetraacetic acid is disodium ethylenediamine tetraacetic acid.

5. A method of prevention and/or treatment of pig dysentery caused by Brachyspira hyodysenteriae, comprising administering to a pig a composition consisting of ethylenediamine tetraacetic acid or a salt thereof acceptable for animal health care purposes.

6. The method of claim 4, further comprising administering an antibiotic to the pig.

7. The method of claim 5, wherein the antibiotic is selected from the group consisting of: lincomycin and tiamulin.

8. The method of claim 4, further comprising administering to the pig an agent selected from the group consisting of: activity-complementing agents; essential oils acceptable for animal health care; tannic acid; and lysozyme.

* * * * *

UNITED STATES PATENT AND TRADEMARK OFFICE
CERTIFICATE OF CORRECTION

PATENT NO. : 8,425,918 B2  
APPLICATION NO. : 12/743791  
DATED : April 23, 2013  
INVENTOR(S) : István Hutás Page 1 of 1

It is certified that error appears in the above-identified patent and that said Letters Patent is hereby corrected as shown below:

In the Claims:

| Col. No. | Line(s) | Edits |
|---|---|---|
| 8 | 46 | Replace "A composition according to claim 1" with --The method of claim 1-- |

Signed and Sealed this  
Ninth Day of July, 2013

Teresa Stanek Rea  
*Acting Director of the United States Patent and Trademark Office*